(12) United States Patent
Midha et al.

(10) Patent No.: US 10,765,610 B2
(45) Date of Patent: *Sep. 8, 2020

(54) ORAL CARE COMPOSITIONS CONTAINING POTASSIUM NITRATE AND PEROXIDE

(71) Applicant: The Procter & Gamble Company, Cincinnati, OH (US)

(72) Inventors: Sanjeev Midha, Mason, OH (US); Lawrence Edward Dolan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 27 days.

This patent is subject to a terminal disclaimer.

(21) Appl. No.: 15/475,169

(22) Filed: Mar. 31, 2017

(65) Prior Publication Data

US 2017/0281486 A1 Oct. 5, 2017

Related U.S. Application Data

(60) Provisional application No. 62/317,409, filed on Apr. 1, 2016.

(51) Int. Cl.

| | | |
|---|---|---|
| *A61Q 11/00* | (2006.01) |
| *A61K 8/21* | (2006.01) |
| *A61K 8/22* | (2006.01) |
| *A61K 6/00* | (2020.01) |
| *A61K 8/25* | (2006.01) |
| *A61K 8/24* | (2006.01) |
| *A61K 8/02* | (2006.01) |
| *A61K 8/19* | (2006.01) |
| *A61K 8/34* | (2006.01) |
| *A61K 8/46* | (2006.01) |
| *A61K 8/81* | (2006.01) |

(52) U.S. Cl.
CPC .............. *A61K 8/22* (2013.01); *A61K 8/0216* (2013.01); *A61K 8/19* (2013.01); *A61K 8/21* (2013.01); *A61K 8/24* (2013.01); *A61K 8/25* (2013.01); *A61K 8/342* (2013.01); *A61K 8/463* (2013.01); *A61K 8/8158* (2013.01); *A61Q 11/00* (2013.01); *A61K 2800/28* (2013.01); *A61K 2800/30* (2013.01); *A61K 2800/412* (2013.01)

(58) Field of Classification Search
CPC . A61Q 11/00; A61K 8/21; A61K 8/22; A61K 6/00

See application file for complete search history.

(56) References Cited

U.S. PATENT DOCUMENTS

| | | | |
|---|---|---|---|
| 4,666,517 A | 5/1987 | Bakar | |
| 5,093,112 A | 3/1992 | Birtwistle et al. | |
| 5,512,278 A | 4/1996 | Mundschenk | |
| 9,005,585 B2 | 4/2015 | Deckner et al. | |
| 2006/0034784 A1 | 2/2006 | Cahen et al. | |
| 2006/0210491 A1 | 9/2006 | Behan et al. | |
| 2009/0246151 A1* | 10/2009 | LeBlanc | A61K 8/0295 424/49 |
| 2014/0308322 A1 | 10/2014 | Midha et al. | |
| 2014/0336308 A1 | 11/2014 | Mateu et al. | |
| 2015/0023890 A1 | 1/2015 | Joziak et al. | |

FOREIGN PATENT DOCUMENTS

| | | |
|---|---|---|
| AU | 2002318865 A1 | 6/2004 |
| EP | 0348560 A1 | 1/1990 |
| WO | WO2007136381 A1 | 11/2007 |
| WO | WO2008042279 A2 | 4/2008 |
| WO | WO2011053877 A2 | 5/2011 |

OTHER PUBLICATIONS

U.S. Appl. No. 15/475,179, filed Mar. 31, 2017, Sanjeev Midha et al.
U.S. Appl. No. 15/475,172, filed Mar. 31, 2017, Sanjeev Midha et al.
U.S. Appl. No. 15/475,170, filed Mar. 31, 2017, Sanjeev Midha et al.
U.S. Appl. No. 15/475,168, filed Mar. 31, 2017, Hoke et al.
International Search Report and Written Opinion for PCT/US2017/025379 dated Jun. 23, 2017.

* cited by examiner

*Primary Examiner* — Tracy Liu
(74) *Attorney, Agent, or Firm* — Parker D. McCrary; Alexandra S. Anoff

(57) ABSTRACT

An oral care composition containing a gel phase, potassium nitrate, a peroxide source, an abrasive, and a fluoride source. Phase separation is not visually perceptible in the oral care composition.

8 Claims, No Drawings

ORAL CARE COMPOSITIONS CONTAINING POTASSIUM NITRATE AND PEROXIDE

FIELD OF THE INVENTION

The present invention relates to an oral care composition. More particularly a stable toothpaste composition containing potassium nitrate and peroxide.

BACKGROUND OF THE INVENTION

Oral care compositions, including toothpaste compositions, can contain fluoride salts, abrasives, and flavors to clean teeth, freshen breath, and maintain the aesthetics and health of the oral cavity, including the teeth and gums. It can also be desirable to include potassium nitrate ($KNO_3$) in oral care compositions to help reduce pain from sensitive teeth (dentinal hypersensitivity) and a peroxide, like hydrogen peroxide, to help whiten teeth.

However, formulating toothpaste compositions with the proper stability and rheology can be very challenging, especially when the composition contains peroxide and potassium nitrate. First, alkali metal salts, like potassium nitrate, catalyze the hydrolysis of peroxide. When peroxide breaks down, it forms oxygen, water, and radicals. The excess gas can cause swelling and bursting of primary packaging and the radicals can cause the entire oral care composition, including the actives and flavors, to break down to a composition with a water like viscosity with decreased efficacy. Furthermore, unacceptable phase separation has been observed in certain toothpastes that $KNO_3$.

As such, there is a need for an improved oral care composition that is stable, has acceptable rheology, and contains peroxide and potassium nitrate.

SUMMARY OF THE INVENTION

An oral care composition comprising: (a) a gel network phase comprising a fatty amphiphile and a secondary surfactant; (b) potassium nitrate; (c) a peroxide source selected from the group consisting of hydrogen peroxide, urea peroxide, calcium peroxide, sodium peroxide, zinc peroxide, polyvinylpyrrolidone peroxide complex or combinations thereof; (d) an abrasive; (e) a fluoride ion source selected from the group consisting of stannous fluoride, sodium fluoride, potassium fluoride, amine fluoride, sodium monofluorophosphate, indium fluoride, amine fluoride, and combinations thereof; wherein phase separation is not visually perceptible as determined by the phase separation method.

An oral care composition comprising: (a) a gel network phase comprising a cold dispersible fatty amphiphile; (b) potassium nitrate; (c) a peroxide source selected from the group consisting of hydrogen peroxide, urea peroxide, calcium peroxide, sodium peroxide, zinc peroxide, polyvinylpyrrolidone peroxide complex or combinations thereof; (d) an abrasive; and a fluoride ion source selected from the group consisting of stannous fluoride, sodium fluoride, potassium fluoride, amine fluoride, sodium monofluorophosphate, indium fluoride, amine fluoride, and combinations thereof; wherein the oral care composition comprises from about 3% to about 17% fatty amphiphile; and wherein phase separation is not visually perceptible as determined by the phase separation method.

DETAILED DESCRIPTION OF THE INVENTION

Oral care compositions can include fluoride, peroxide, potassium nitrate, abrasives, flavors, and other ingredients to provide benefits like reducing plaque and tartar, reducing pain from sensitive teeth, preventing cavities, preventing and reversing gingivitis, building protection against sensitivity, freshening bad breath, and whitening teeth. Some consumers are particularly interested in a product that contains both potassium nitrate to help alleviate dentinal hypersensitivity and peroxide to help whiten teeth.

However, formulating toothpaste compositions with peroxide and potassium nitrate can be challenging because many metals, like potassium nitrate, can catalyze hydrolysis of peroxide. Peroxide can also be incompatible with other compositions frequently found in oral care products, such as precipitated silica abrasives and certain polymers. When peroxide breaks down, it forms oxygen, water, and radicals. The excess gas can cause swelling and bursting of primary packaging and the radicals can cause the entire oral care composition, including the actives and flavors, to break down to a composition with a water like viscosity with decreased efficacy.

In order to improve rheology, oral care products can include a gel network phase as a structurant. The gel network phase can include a fatty amphiphile, such as a fatty alcohol, and a secondary surfactant. Including a gel network phase can also provide a unique brushing experience. For instance, toothpaste that contains a gel network phase can have excellent foaming and the foam may not easily break down during brushing, even when it is used with an electric toothbrush. Also, some commercially available toothpastes can feel harsh and can irritate a user's mouth, however, toothpastes containing gel networks can feel smooth and are generally non-irritating. Additionally, after brushing, the mouth not only feels fresh and clean, but a user's teeth can feel especially smooth and the smoothness can persist throughout the day because the amount of biofilm that builds on the teeth between brushings can be significantly reduced.

However, it has been observed that toothpastes containing a gel network phase and an effective level of $KNO_3$ can separate into phases, where the water separates from the gel/paste phase, which is unacceptable. While not wishing to be bound by theory, it is hypothesized that the salt interrupts the structure of the gel network, which results in the phase separation. Phase separation in toothpaste is particularly problematic, as toothpaste is generally dispensed from a narrow tube with a small opening, which makes it very difficult for a consumer to stir or otherwise mix the toothpaste to reincorporate the separated phase.

The toothpaste composition can contain a gel network phase, greater than about 1% hydrogen peroxide, an effective amount of potassium nitrate, a fatty amphiphile, and a secondary surfactant. The toothpaste composition can also contain a peroxide stable polymer, including but not limited to a polymer containing 2-acrylamido-2-methylpropane sulfonic acid (AMPS) polymers, copolymers and crosspolymers. The toothpaste composition can also contain an abrasive polishing material that is compatible with peroxide. The abrasive polishing material can be selected from the group consisting of polyorganosilsequioxane particles, calcium pyrophosphate, dicalcium phosphosphate, calcium phosphate, strontium carbonate, barium sulfate, fused silica, or combinations thereof. The abrasive polishing material is substantially free (i.e., less than 0.1 wt %, or less than 0.05 wt %, or less than 0.01 wt %, or no detectable amounts of those materials) of precipitated silica.

The toothpaste composition can be phase stable and phase separation may not be visually perceptible, as determined by the Phase Separation Method, described hereafter.

The composition may not have a visually perceptible phase separation. The term "visually perceptible" as used herein means that a human viewer can visually discern a phase separation with the unaided eye (excepting standard corrective lenses adapted to compensate for near-sightedness, farsightedness, or stigmatism, or other corrected vision) in lighting at least equal to the illumination of a standard 100 watt incandescent white light bulb at a distance of approximately 18 inches.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

The composition can contain, consist of, or consist essentially of, the essential elements and limitations of the invention described herein, as well as any additional or optional ingredients, components, or limitations described herein or otherwise useful in oral care compositions.

As used herein, the word "include," and its variants, are intended to be non-limiting, such that recitation of items in a list is not to the exclusion of other like items that may also be useful in the materials, compositions, devices, and methods of this invention.

As used herein, the articles "a" and "an" are understood to mean one or more of the material that is claimed or described, for example, "an abrasive" or "a surfactant".

As used herein, the word "or" when used as a connector of two or more elements is meant to include the elements individually and in combination; for example X or Y, means X or Y or both.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. The oral care compositions can include toothpaste, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dispenser", as used herein, means any pump, tube, or container suitable for dispensing compositions such as toothpastes.

The term "effective amount or "effective level" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. An "effective amount" can mean that at least 0.01% of the material, by weight of the composition, alternatively at least 0.1%. An "effective level" of potassium nitrate can be about 5%.

The term "secondary surfactant" as used herein means a surfactant other than a fatty amphiphile. Various types of suitable surfactants are listed below. There may be more than one secondary surfactants. There can be at least one secondary surfactant in the gel network phase and there may be another surfactant in the oral carrier phase.

The term "teeth", as used herein, refers to natural teeth as well as artificial teeth or dental prosthesis.

The term "toothpaste", as used herein, includes tooth or subgingival paste, gel, or liquid formulations unless otherwise specified. The toothpaste composition may be a single phase composition or may be a combination of two or more separate toothpaste compositions. The toothpaste composition may be in any desired form, such as deep striped, surface striped, multilayered, having a gel surrounding a paste, or any combination thereof. Each toothpaste composition in a toothpaste comprising two or more separate toothpaste compositions may be contained in a physically separated compartment of a dispenser and dispensed side-by-side. As Herein, the terms "toothpaste" and "dentifrice" can be used interchangeably.

The term "water", as used herein, refers to deionized water, unless otherwise specified.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The toothpaste composition can include a gel network in combination with an effective level of $KNO_3$ and at least 1% peroxide. When formulating a toothpaste, it is important that the toothpaste has the proper rheology, so it is acceptable to consumers. The composition must not be too thick so it can easily dispense out of a tube but thick enough to stand up on a toothbrush without sinking into the bristles. Also, many consumers rinse the toothbrush after applying a nurdle of toothpaste and the nurdle cannot wash away when the water is applied from a faucet. The viscosity of the oral composition must remain stable over time as not to continue to thicken so the oral composition remains easy to dispense during the shelf life. Once dispensed from a container, the oral composition should not be stringy or sticky as to be messy for a consumer to use. The oral composition must also easily disperse once in the mouth and foam. It is also desired that the oral composition not stick to a sink or leave difficult to remove residue. In addition to balancing the viscosity and shear thinning to formulate acceptable rheology, the oral composition must also keep active ingredients including fluoride salts, potassium nitrate stable, and peroxide stable and available so the product is efficacious.

It can be desirable to formulate the composition with a gel network phase, in order to improve rheology, mouthfeel, and possibly stability of actives. However, when the composition contains both $KNO_3$ and peroxide, the gel network can be carefully formulated, since $KNO_3$ can catalyze the hydrolysis of peroxide and synresis has been observed with gel networks toothpastes containing $KNO_3$.

The amount of fatty amphilphile and/or the amount of secondary surfactant can be increased to improve phase stability. As used herein, "fatty amphiphile" refers to a compound having a hydrophobic tail group and a hydrophilic head group which does not make the compound water soluble (immiscible), wherein the compound also has a net neutral charge at the pH of the oral composition. The fatty amphiphile can be selected from the group consisting of fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, phospholipids, and combinations thereof. Suitable fatty amphiphiles include a combination of cetyl alcohol and stearyl alcohol. The fatty amphiphile can be a fatty alcohol.

The fatty amphiphile can be a fatty alcohol. The fatty amphiphiles can include a cetyl alcohol and/or stearyl alcohol. The oral care compositions may contain a fatty amphiphile in an amount greater than about 10%, greater than about 11%, greater than about 13%, greater than about 14%, greater from about 14.5%, greater than about 15%, greater than about 15.5%, and/or in greater than about 16%. The oral care composition may contain a fatty amphiphile in an amount less than about 40%, less than about 35%, less than about 30%, less than about 25%, less than about 22%, less than about 20%, less than about 19%, less than about 18%, and/or less than about 17%. The oral care composition may contain a fatty amphiphile in an amount from about 3% to about 30%, from about 4% to about 28%, from about 5% to about 26%, in from about 7% to about 25%, from about 8% to about 23%, from about 10% to about 21%, from about 12% to about 20%, from about 13% to about 19%, from about 14% to about 18%, and/or from about 15% to about 17%.

The toothpaste can be phase stable and can contain a gel network phase, which can include a cold dispersible fatty amphiphile and the composition can contain less than about 14% fatty amphiphile.

It can be desirable to use less fatty amphiphile, since some consumers find that if the fatty amphiphile level is too high, the toothpaste may have less desirable aesthetics include suboptimal taste and flavor display and a greasy feeling in the oral cavity and on the lips. The toothpaste can be phase stable and can contain a gel network phase, an effective level of potassium nitrate, greater than about 1% peroxide, and the toothpaste can contain less than about 14% fatty amphiphiles. The oral care composition can contain a cold dispersible fatty amphiphile.

The composition can contain a cold dispersible fatty amphiphile. The composition can contain from about 1% to about 20% cold dispersible fatty amphiphile, from about 3% to about 17%, from about 5% to about 15%, from about 7% to about 13%, from about 8% to about 12%, and/or from about 9% to about 11.5%. The composition can contain from about 0.1% to about 5% cold dispersible fatty amphiphile, from about 0.5% to about 3%, from about 0.75% to about 2.5%, and from about 1% to about 2%. The composition can contain greater than about 0.5% cold dispersible fatty amphiphile, greater than about 1%, greater than about 3%, greater than about 5%, greater than about 7%, greater than about 8%, and/or greater than about 9%.

The cold dispersible fatty amphiphile can have a melting point greater than about 10° C., greater than about 25° C., greater than about 30° C., greater than about 35° C., greater than about 40° C., greater than about 45° C., greater than about 55° C. The melting point of the cold dispersible fatty amphiphile can be from about 20° C. to about 100° C., from about 30° C. to about 90° C., from about 35° C. to about 85° C., from about 40° C. to about 80° C., from about 45° C. to about 75° C., from about 50° C. to about 70° C., from about 55° C. to about 65° C., and/or from about 57° C. to about 67° C. Melting point can be determined by USP (United States Pharmacopeia) Testing Method <741>, Class 1a, Apparatus I.

The cold dispersible fatty amphiphile can contain straight or branched carbon chains from about C8 to about C25 and from about C12 to about C22.

The cold dispersible fatty amphiphile can contain 40% cetyl alcohol, 40% stearyl alcohol, 10% sodium lauryl sulfate (SLS), and 10% sodium acrylate/sodium acryloyl dimethyl taurate copolymer.

The cold dispersible fatty amphiphile can contain from about 40% to about 98% fatty amphiphile, from about 50% to about 95% fatty amphiphile, in from about 60% to about 90% fatty amphiphile, from about 70% to about 85% fatty amphiphile, and/or from about 75% to about 80% fatty amphiphile. The fatty amphiphile can be a fatty alcohol. The cold dispersible fatty amphiphile can contain one fatty alcohol and/or fatty amphiphile, two different fatty alcohols and/or fatty amphiphile, three different fatty alcohols and/or fatty amphiphile, four different fatty alcohols and/or fatty amphiphiles, and/or five or more different fatty alcohols and/or fatty amphiphiles. The cold dispersible fatty amphiphile can contain a fatty alcohol selected from the group consisting of cetyl alcohol, stearyl alcohol, and combinations thereof. The cold dispersible fatty amphiphile can contain two fatty alcohols where the first fatty alcohol is cetyl alcohol and the second fatty alcohol is stearyl alcohol. The ratio of first fatty amphiphile to second fatty amphiphile can be about 1:5 to about 5:1, from about 1:4 to about 4:1, from about 1:3 to about 3:1, from about 1:2 to about 2:1, and/or the ratio can be about 1:1.

The cold dispersible fatty amphiphile can contain from about 1% to about 40% surfactant, from about 5% to about 30%, from about 7% to about 20%, and/or from about 10% to about 15%. The surfactant can be an anionic surfactant. The surfactant can be sodium lauryl sulfate.

The cold dispersible fatty amphiphile can contain from about 1% to about 40% polymer, from about 5% to about 30%, from about 7% to about 20%, from about 8% to about 15%, i from about 9% to about 14%, from about 10% to about 12%. The polymer can be an anionic polymer. The polymer is an AMPS polymer, which can have the following structure:

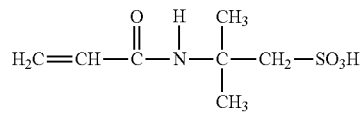

The polymer can be a polymer containing the following monomer unit:

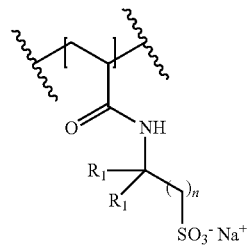

where $R_1$ is independently selected from $C_1$ to $C_4$ (lower alkyls) and n=1-3.

The ratio of surfactant to polymer in the cold dispersible fatty amphiphile is about 1:10 to about 10:1, from about 1:7 to about 7:1, from about 1:5 to about 5:1, from about 1:3 to about 3:1, and the ratio can be about about 1:1.

The ratio of fatty amphiphile to surfactant or polymer in the cold dispersible fatty amphiphile can be from about 1:1 to about 30:1, from about 2:1 to 25:1, in from about 3:1 to about 20:1, from about 4:1 to about 15:1, from about 5:1 to about 10:1, from about 6:1 to about 9:1, from about 7:1 to about 8:1, and/or about 8:1.

The ratio of fatty amphiphile to surfactant and polymer in the cold dispersible fatty amphiphile can be 1:1 to 15:1, from about 2:1 to 10:1, from about 3:1 to about 8:1, from about 4:1 to about 6:1, and/or about 4:1.

Since peroxide can be unstable, it may not be desirable to combine peroxide with particular polymers, including carrageenan. The oral care composition can be free of or substantially free of carrageenan. The composition can be free of or substantially free of carboxymethyl cellulose. The composition can be free of or substantially free of xanthan gum. The composition can contain less than about 1%, less than about 0.5%, less than about 0.25%, less than about 0.1%, less than about 0.05%, less than about 0.01%, less than about 0.001%, and/or less than about 0.0001% polymer selected from the group consisting of carrageenan, carboxymethyl cellulose, xanthan gum, and combinations thereof.

The oral care composition can contain an AMPS polymer, co-polymer, and/or crosspolymer, as described above. Non-limiting examples of polymers, copolymers and crosspolymers synthesized from AMPS can include hydroxyethyl acrylate/sodium acryloyldimethyl taurate copolymer (commercially available as Sepinov™ EMT-10 from SEPPIC S.A.), ammonium acryloyldimethyl taurate/vinyl pyrrolidone copolymer (commercially available as Aristoflex® AVC from Clariant International LTD, Muttenz, Switzerland), ammonium acryloyldimethyltaurate/beheneth-25 methacrylate crosspolymer (commercially available as Aristoflex® HMB, Clariant International LTD), sodium acrylate/sodium acryloyldimethyltaurate copolymer (a component of Sepigel EG and Simulgel SMS 88, SEPPIC S.A.), acrylamide/sodium acryloyldimethyltaurate copolymer (a component of Simulgel 600 and Simulgel 600 PHA, SEPPIC S.A.), polyacrylate crosspolymer-6 (commercially available as SepiMAX™ ZEN from SEPPIC S.A.), and combinations thereof.

The oral care composition can contain polyacrylate crosspolymer-6 (commercially available as SepiMAX™ ZEN from SEPPIC S.A., a subsidiary of the Air Liquide group, Puteaux Cedex, France). The molecular structure of polyacrylate crosspolymer-6 is shown below.

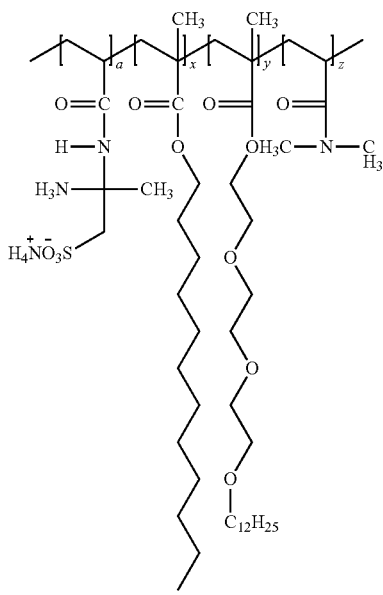

Polyacrylate crosspolymer-6 is a copolymer of Ammonium 2-methyl-2-[(1-oxo-2-propenyl)amino]-1-propanesulfonate, N,N, Dimethyl-2-acrylamide, Poly(oxy-1,2-ethanediyl), alpha-(2-methyl-1-oxo-2-propenyl0-omega-(dodecyloxy) and Methyl-2-propenoic acid dodecyl ester monomers.

The oral care composition can contain from about 0.1% to about 10% AMPS polymer, copolymer, or crosspolymer, from about 0.5% to about 7%, from about 1% to about 5%, from about 1.2% to about 4%, and/or from about 1.6% to about 3.5%. The oral care composition can contain from about 0.01% to about 5% AMPS polymer, copolymer, or crosspolymer, from about 0.1% to about 3%, from about 0.25% to about 1.5%, from about 0.3% to about 1%, and/or in from about 0.5% to about 0.8%.

The composition can contain another salt, for instance pyrophosphates, which can help control tartar, in addition to or instead of potassium nitrate.

Toothpastes that contain both gel networks, $KNO_3$, and peroxide can be enjoyed by consumers. They are used the same way as regular toothpaste. For instance, the American Dental Association recommends brushing at least twice a day for two minutes with a soft-bristled brush. Then the brush is placed in a user's mouth at a 45-degree angle to the gums and gently moved back and forth in short (tooth-wide) strokes. The outer surfaces, inner surfaces, and the chewing surfaces of the teeth can be brushed. A user can also brush her tongue to remove bacteria and keep her breath fresh. The toothpaste containing gel networks can be combined with other oral care regiments such as flossing, mouthwashes, whitening regimens, and regular visits to the dentist for professional cleanings and oral exams.

The user can dispense the toothpaste from the container, which can be a metal or plastic tube. When dispensed, the first thing that a consumer may notice is the rheology of the toothpaste containing a gel network. The toothpaste can easily dispense from the container. The toothpaste can dispense cleanly out of the container onto the brush without being stringy. The nurdle can be smooth, not lumpy, and is thick enough that it stands up on the brush without sinking into the bristles.

Next, the consumer will brush her teeth. She may find that the toothpaste feels especially smooth in her mouth and the toothpaste is not irritating. Again, she may notice that the toothpaste is not stringy, but it is easily spread throughout her entire mouth. The user may notice that the toothpaste foams. The foaming can feel unique, as it builds and/or is maintained during brushing, which can last two minutes (as recommended by the American Dental Association®) or longer. The foam is not dense and heavy, like some products that may overwhelm the consumer. Furthermore, users may notice that foam from some current commercially available toothpastes breaks down and becomes thin and watery and causes a mess during brushing, especially if the user is brushing with an electric toothbrush. However, in toothpaste that contains a gel network phase, the foam can gently build during brushing and be very pleasant. Users may also notice that the flavor pleasantly builds intensity during brushing. After expectorating the toothpaste containing a gel network, the user may find it easily removed from the sink, for instance in the toothpaste can be removed by simply turning on the water for the sink. The toothpaste containing gel networks may not stain the sink or countertop or the user's mouth or lips.

Consumers may find that these desirable properties are maintained or substantially maintained for the entire shelf life of the product. The oral care composition may not significantly thicken during the shelf life. The actives, including the fluoride component and the KNO₃ and/or peroxide, can be relatively stable and present at effective levels at the end of the shelf life. The toothpaste can also keep the actives available so they can deliver a therapeutic effect while brushing.

After use, a consumer may find that her teeth feel especially smooth and she may notice that this smoothness lasts for hours or even throughout the entire time between brushing. It may be determined that less biofilm forms over her teeth between brushing and consequently and therefore users of this product may have less plaque buildup over time. After using the toothpaste containing gel networks for some time (even a short period of time, such as a few brushings), a user may find that her gums are less sensitive and may have reduced bleeding. A user may also have more pleasant dental checkups because less plaque needs to be removed and her gums are not as sensitive. The user may believe that her teeth look especially white as well and the teeth may become whiter either by removing extrinsic stains or intrinsically whitening teeth. The user may have a fresh clean feeling in her mouth for an extended period of time. The user may have fresh breath for an extended period of time. The user may notice that her teeth are less sensitive.

The toothpaste composition has a shelf life of at least about 1 year, at least about 1.5 years, at least about 2 years, at least about 2.5 years, and/or at least about 3 years.

The oral care composition can contain one or more secondary surfactants. The secondary surfactant is typically water soluble or miscible in the solvent or oral carrier. Suitable secondary surfactants include anionic, zwitterionic, amphoteric, cationic, and nonionic secondary surfactants. The anionic secondary surfactants such as sodium lauryl sulfate, can be used. The composition can contain from about 1% to about 15% anionic secondary surfactant, from about 2% to about 10%, from about 3% to about 8.5%, from about 4% to about 8%, from 5% to about 7.5%, and/or from about 6% to about 7%. The secondary surfactants may be a combination of more than one type of secondary surfactants, such as an anionic and nonionic secondary surfactant. Suitable solvents for the present invention can include water, edible polyhydric alcohols such as glycerin, diglycerin, triglycerin, sorbitol, xylitol, butylene glycol, erythritol, polyethylene glycol, propylene glycol, and combinations thereof.

Secondary surfactants may include anionic surfactants such as organophosphate, which include alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one example selected from linear or branched, alkyl or alkenyl group of from 1 to 22 carbon atoms, optionally substituted by one or more phosphate groups; alkoxylated alkyl or alkenyl, (poly)saccharide, polyol or polyether group.

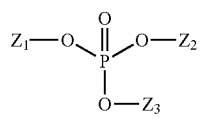

Some other organophosphate agents include alkyl or alkenyl phosphate esters represented by the following structure:

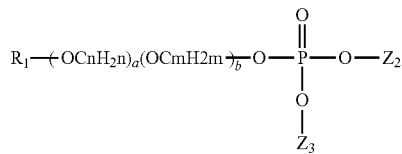

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a (OCmH2m)b-group. Examples of suitable agents include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. The alkyl phosphate is polymeric. Polymeric alkyl phosphates can include those containing repeating alkoxy groups as the polymeric portion, in particular 3 or more ethoxy, propoxy isopropoxy or butoxy groups.

Zwitterionic or amphoteric secondary surfactants useful in the present invention can include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric secondary surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N, N-dimethyl ammonio) acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these secondary surfactants are soapy, bitter, chemical, or artificial. The composition can contain from about 0.1% to about 6% amphoteric secondary surfactant, from about 0.5% to about 4%, from about 0.75% to about 2%, and/or about 1%.

Additional suitable polymeric organophosphate agents can include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/ PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 or TRPV1 agonists.

Cationic secondary surfactants useful in the present invention can include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421 to Briner et al. Certain cationic secondary surfactants can also act as germicides in the oral care compositions disclosed herein.

The oral care composition can have a viscosity from about 5 BKUs to about 70 BKUs, from about 10 BKUs to about 45 BKUs, from about 12 BKUs to about 40 BKUs, from about 15 BKUs to about 35 BKUs, from about 18 BKUs to about 30 BKUs, from about 20 BKUs to about 28 BKUs, and/or from about 22 BKUs to about 25 BKUs. The oral care compositions can have a viscosity from about 10 BKUs to about 200 BKUs, from about 20 BKUs to about 175 BKUs from about 30 BKUs to about 150 BKUs, and/or from about 50 BKUs to 100 BKUs. The oral care compositions can have a viscosity from about 10 BKUs to about 200 BKUs, from about 20 BKUs to about 175 BKUs from about 30 BKUs to about 150 BKUs, and/or from about 50 BKUs to 100 BKUs. Viscosity can measured by the Brookfield Viscosity Test as described hereafter.

The oral care composition can have a shelf life, when stored below 40° C., of at least 6 months, at least 1 year, at least 18 months, at least 2 years, at least 30 months, and/or in at least 3 years. The shelf life can be from about 6 months to about 5 years, from about 1 year to about 3 years, and/or from about 1.5 years to about 2.5 years.

The oral care composition can have a pH from about 2 to about 10, from about 4 to about 9, from about 5 to about 8, and/or from about 6 to about 7.5. pH can be measured using the pH Test Method as described hereafter.

Actives and other ingredients may be categorized or described herein by their cosmetic benefit, therapeutic benefit, or their postulated mode of action or function. However, it is to be understood that the active and other ingredients useful herein can, in some instances, provide more than one cosmetic benefit, therapeutic benefit, function, or can operate via more than one mode of action. Therefore, classifications herein are made for the sake of convenience and are not intended to limit an ingredient to the particularly stated function(s) or activities listed.

It is common to have a fluoride compound present in toothpastes and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 to Briner et al. and U.S. Pat. No. 3,678,154 to Widder et al.

A metal salt includes zinc salts, stannous salts, potassium salts, copper salts, alkali metal bicarbonate slats, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 5%, by total weight of the oral care composition. Some metal salts which may be used in the present invention, such as zinc chloride, zinc citrate, copper gluconate, and zinc gluconate, are also associated with an off taste described as dirty, dry, earthy, metallic, sour, bitter, and astringent.

Stannous salts include stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients used to stabilize the stannous may be included, such as the ingredients described in Majeti et al. and Prencipe et al.

Zinc salts include zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts can include potassium nitrate, potassium citrate, potassium oxalate, potassium bicarbonate, potassium acetate, potassium chloride, and combinations thereof. The composition can contain from about 0.05% to about 15% potassium nitrate, from about 0.5% to about 10%, from about 1% to about 8%, from about 2% to about 7%, from about 3% to about 6%, and from about 4% to about 5.5%, by total weight of the oral care composition.

The copper salt can be selected from copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. The copper salt can be selected from copper gluconate, copper acetate, copper glycinate, and combinations thereof.

Sweeteners can include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N-[N-[3-(3-hydroxy-4-methoxyphenyl)propyl]-L-α-aspartyl]-L-phenylalanine 1-methyl ester, N-[N-[3-(3-hydroxy-4-methoxyphenyl)-3-methylbutyl]-L-α-aspartyl]-L-phenylalanine 1-methyl ester, N-[N-[3-(3-methoxy-4-hydroxyphenyl)propyl]-L-α-aspartyl]-L-phenylalanine 1-methyl ester, salts thereof, and combinations thereof.

Rebiana can be a steviolglycoside from Cargill Corp., Minneapolis, Minn., which is an extract from the leaves of the Stevia rebaudiana plant (hereinafter referred to as "Rebiana"). This is a crystalline diterpene glycoside, about 300× sweeter than sucrose. Suitable stevioglycosides which may be combined can include rebaudioside A, rebaudioside B, rebaudioside C, rebaudioside D, rebaudioside E, rebaudioside F, dulcoside A, dulcoside B, rubusoside, stevioside, or steviolbioside. The combination of high-potency sweeteners can comprise rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%, by total weight of the oral care composition.

Carrier materials can include water, glycerin, sorbitol, polyethylene glycols including those having a molecular weight of less than about 50,000, propylene glycol and other edible polyhydric alcohols, ethanol, or combinations thereof. The oral care compositions of the present invention include from about 5% to about 80%, by weight of the composition, of a carrier material. The compositions can contain carrier materials in an amount of from about 10% to about 40%, by total weight of the oral care composition.

The composition can contain from about 15% to about 95% water, from about 20% to about 85%, from about 25% to about 70%, from about 28% to about 60%, from about 30% to about 50%, from about 31% to about 48%, from about 32% to about 45%, and/or from about 33% to about 43%. The composition can contain from about 1% to about 20% water, from about 2% to about 15% water, from about 3% to about 10% water, and/or from about 4% to about 8% water. The composition can contain greater than about 5% water, greater than about 8%, greater than about 10%, greater than about 15%, greater than about 20%, greater than about 25%, greater than about 30%, greater than about 40%, and/or greater than about 50%.

Antimicrobial agents include quaternary ammonium compounds. Those useful in the present invention can include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Examples of pyridinium quaternary ammonium compounds can include bis[4-(R-amino)-1-pyridinium]alkanes as disclosed in U.S. Pat. No. 4,206,215, Jun. 3, 1980, to Bailey and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents can include chlorhexidine, and flavor oils such as thymol. The antimicrobial agent can include triclosan.

The compositions of the present invention may contain antimicrobial agents in an amount of from about 0.035% or more, from about 0.1% to about 2.0%, from about 0.045% to about 1.0%, or from about 0.05% to about 0.10%, by total weight of the oral care composition. The compositions can include from about 0.001% to about 1.5% antimicrobial agent, from about 0.005% to about 0.8%, from 0.01% to about 0.7%, from about 0.05% to about 0.5%, and/or from about 0.1% to about 0.3%.

Non-limiting examples of peroxide (peroxygen) compounds can include hydrogen peroxide, urea peroxide, calcium peroxide, sodium peroxide, zinc peroxide, polyvinylpyrrolidone peroxide complex or combinations thereof. The composition can contain greater than about 0.05% peroxide, greater than about 0.5%, greater than about 0.75%, greater than about 1%, greater than about 1.25%, greater than about 1.5%, greater than about 1.75%, greater than about 2%, greater than about 2.25%, greater than about 2.5%, greater than about 2.75%, greater than about 2.85%, greater than about 2.9%, greater than about 2.95%, greater than about 3%, greater than about 4%, greater than about 5%, and greater than about 6%. The composition can contain from about 0.01% to 10% peroxide, from about 0.05% to about 8%, from about 0.1% to about 5%, from about 0.5% to about 4.5%, from about 1% to about 4%, from about 1.5% to about 3.5%, and/or from about 2% to about 3%. The composition can contain from about 1% to about 10% peroxide, from about 2% to about 8% peroxide, from about 3% to about 7% peroxide, and/or from about 4% to about 6% peroxide. The composition can contain from about 0.01% to about 6% peroxide, from about 0.05% to about 3%, and/or from about 0.1% to about 1%.

The composition can be free of or substantially free of a peroxide component, including but not limited to hydrogen peroxide.

The oral care composition can include bleaching agents. Bleaching agents can include perborates, percarbonates, peroxyacids, persulfates, peracids, peracid precursor systems, and preformed peracids and combinations thereof. One example of a percarbonate can include sodium percarbonate. An example of a persulfate can include oxones.

The compositions of the present invention may contain bleaching agents in an amount of from about 0.01% to about 30%, from about 0.1% to about 10%, or from about 0.5% to about 5%, by total weight of the oral care composition.

Some flavors that may be used in oral care compositions are mint oils, and components thereof, wintergreen, clove bud oil, cassia, sage, parsley oil, marjoram, lemon, orange, propenyl guaethol, heliotropine, cis-4-heptenal, diacetyl, methyl-ρ-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenyl-ethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, isopulegol, piperitone, or combinations thereof. Generally suitable flavoring ingredients are chemicals with structural features and functional groups that are less prone to redox reactions. These include derivatives of flavor chemicals that are saturated or contain stable aromatic rings or ester groups.

Flavors can be present in an amount of from about 0.4% to about 5%, by total weight of the oral care composition, alternatively from about 0.8% to about 4%, alternatively from about 1% to about 3.5%, and alternatively from about 1.5% to about 3%. It can be desirable to have a flavor composition at less than about 4%, by total weight of the oral care composition, alternatively less than about 3.5%, alternatively in another example less than about 3%, and alternatively less than about 2%.

Dentifrice compositions of the present invention may also comprise an anti-calculus agent, which may be present from about 0.05% to about 50%, by weight of the dentifrice composition, alternatively from about 0.05% to about 25%, and alternatively from about 0.1% to about 15%. The compositions can contain an amount of anti-calculus agent that is effective in tartar control effective. The amount of pyrophosphate salt may be from about 1.5% to about 15%, alternatively from about 2% to about 10%, or alternatively from about 3% to about 8%. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) mono-acid, potassium hydrogen phosphate, sodium hydrogen phosphate, and alkali metal (e.g. sodium) hexametaphosphate, and mixtures thereof. The composition can contain from about 1% to about 30% polyphosphate salts, alternatively from about 5% to about 25%, alternatively from about 10% to about 20%, alternatively from about 11% to about 15%, and alternatively from about 13%. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azocyclohexane-2,2-diphosphonic acid, azacyclopentane-2,2-diphosphonic acid, N-methyl-azacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Some colorants that may be used in oral care compositions include D&C Yellow No. 10, FD&C Blue No. 1, FD&C Red No. 40, D&C Red No. 33 and combinations thereof. The composition can comprise colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the user. Sensates are generally present in an amount of from about 0.001% to about 2%, by weight of the oral care composition. The most well-known cooling sensate compound can be menthol, particularly L-menthol, which is found naturally in peppermint and spearmint oils notably of Mentha piperita, Mentha arvensis L and Mentha viridis L. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there can be no cooling effect for the other isomers. For example, d-neomenthol is reported to have a cooling threshold of about 25,000 ppb and 1-neomenthol about 3,000 ppb.

Of the menthol isomers the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

Among synthetic coolants, many are derivatives of or are structurally related to menthol, for example containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), WS-12 (1R* ,2S*)-N-(4-Methoxyphenyl)-5-methyl-2-(1-methylethyl)cyclohexanecarboxamide] and WS-14 (N-tertbutyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425 to Amano et al. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted p-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)p-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,917,613; 3,991,178; 5,703,123; 5,725,865; 5,843,466; 6,365,215; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5 -MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630 and phosphine oxides as reported in U.S. Pat. No. 4,070,496.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

The abrasive polishing material can have a BET surface area greater than about 5 $m^2/g$, alternatively greater than about 10 $m^2/g$, alternatively greater than about 15 $m^2/g$, in alternatively greater than about 18 $m^2/g$, alternatively greater than about 25 $m^2/g$, alternatively greater than about 30 $m^2/g$, alternatively greater than about 35 $m^2/g$, alternatively greater than about 40 $m^2/g$, and alternatively greater than about 50 $m^2/g$. The BET surface area of the abrasive polishing material can be from about 5 $m^2/g$ to about 30 $m^2/g$, alternatively from about 10 $m^2/g$ to about 200 $m^2/g$, alternatively from about 20 $m^2/g$ to about 150 $m^2/g$, alternatively from about 25 $m^2/g$ to about 100 $m^2/g$, alternatively from about 30 $m^2/g$ to about 75 $m^2/g$, alternatively from about 35 $m^2/g$ to about 60 $m^2/g$, alternatively from about 38 $m^2/g$ to about 50 $m^2/g$, and alternatively from about 40 $m^2/g$ to about 45 $m^2/g$. The precipitated silica can have a BET surface area from about 19 $m^2/g$ to about 55 $m^2/g$ and alternatively from about 19 $m^2/g$ to about 35 $m^2/g$. In The silica can have a BET surface area from about 10 $m^2/g$ to about 80 $m^2/g$, alternatively from about 20 $m^2/g$ to about 70 $m^2/g$, alternatively from about 25 $m^2/g$ to about 50 $m^2/g$, or alternatively from about 30 $m^2/g$ to about 45 $m^2/g$. BET surface area is determined by BET nitrogen absorption method of Brunaur et al., J. Am. Chem. Soc., 60, 309 (1938). See also U.S. Pat. No. 7,255,852 to Gallis.

The abrasive polishing material can have an LOD of about 1% to about 10%, in alternatively from about 3% to about 7%, alternatively from about 4% to about 6.75%, and alternatively from about 5.6% to about 6.1%. The LOD is less than about 7%, alternatively less than about 6.5%, and alternatively less than about 6.25%. The abrasive polishing material can have an LOI from about 2% to about 10%, alternatively from about 3% to about 7%, alternatively from about 4% to about 6%, and alternatively about 5.1%. The LOI can be greater than about 3%, alternatively greater than about 4%, and alternatively greater than about 5%. The sum of LOD and LOI can be from about 5% to about 20%, alternatively from about 7% to about 17%, alternatively from about 8% to about 15%, alternatively from about 9% to about 14%, and alternatively from about 10% to about 12.5%. Silicas with less than about 5% bound and free water may be considered substantially non-hydrated. The total bound and free water can be calculated by totaling two measurements, loss on drying (LOD) and loss on ignition (LOI). For loss on drying, performed first, a sample may be dried at 105° C. for two hours, the weight loss being the free water. For loss on ignition, the dried sample then may be heated for one hour at 1000° C., the weight loss being the bound water. The sum of the LOD and LOI represents the total bound and free water in the original sample.

Typical abrasive polishing materials can include silicas including gels and precipitates; aluminas; phosphates including orthophosphates, polymetaphosphates, and pyrophosphates; and mixtures thereof. Specific examples include silicone microspheres such as polyorganosilsesquioxane particles, dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510. In certain examples, if the oral composition or particular phase comprises a polyphosphate having an average chain length of about 4 or more, calcium containing abrasives and alumina are not preferred abrasives. In certain examples, the composition is substantially free of silica.

The composition can contain a silica abrasive. Silica abrasive polishing materials that may be used in the present invention, as well as other abrasives, generally have an average particle size ranging between about 0.1 to about 30 µm or from about 5 to about 15 µm. The abrasive can be precipitated silica or silica gels such as the silica xerogels described in Pader et al., U.S. Pat. No. 3,538,230 and DiGiulio, U.S. Pat. No. 3,862,307. Silica xerogels marketed under the trade name "Syloid" by the W.R. Grace & Company, Davison Chemical Division, Augusta, Ga. may be used. Also precipitated silica materials such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in U.S. Pat. Nos. 4,340,583; 5,589,160; 5,603,920; 5,651,958; 5,658,553; and 5,716,601.

The composition can be substantially free of a silica abrasive.

The abrasive can include polymethyl organosiloxane particles. The types of polymethyl organosiloxane particles useful in the oral care compositions of the present invention are described in more detail in U.S. Pat. No. 9,017,647. It may be advantageous to select an abrasive containing polymethyl organosiloxane particles because they are less reactive with ingredients commonly found in oral care compositions, including oral care actives such as peroxide.

The abrasive can include calcium pyrophosphate. The abrasive can include poly(methyl methacrylate), calcium carbonate, dicalcium phosphate, and/or barium sulfate.

Thickening material or binders may be used to provide a desirable consistency to the oral care compositions of the present invention.

Thickening materials can include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. Thickening materials can be used in an amount from about 0.1% to about 15%, by weight of the oral care composition. Thickening materials can be used in an amount from about 0.01% to about 3%, alternatively from about 0.1% to about 2%, alternatively from about 0.2% to about 1%, alternatively from about 0.25% to about 0.75%, alternatively from about 0.27% to about 0.5%, and alternatively from about 0.3% to about 0.4%. The oral care compositions can also contain binders that can also adjust formulation texture and mouth feel.

The thickening agent can include the addition of polymers of acrylic acid crosslinked with an unsaturated polyfunctional agent such as a polyallyl ether of sucrose. These carboxy vinyl polymers have the CTFA (Cosmetic, Toiletry and Fragrance Association) adopted name of "carbomer." A carbomer can include negatively charged polyelectrolytes, such as Carbomer 956 (available from Lubrizol Corporation, Wickliffe, Ohio). The carbomer can be selected from the group consisting of acrylates/C10-30 alkyl acrylate crosspolymer, sodium polyacrylate; polyacrylate-1 Crosspolymer (available from Lubrizol); polyacrylate Crosspolymer-11 (available from Clariant, Inc., Louisville, Ky., USA), acrylates/C10-30 alkyl acrylate crosspolymer, and combinations thereof. The carbomer can be Carbomer 956. The composition can contain from about 0.1% to about 15% carbomer, alternatively from about 0.3% to about 10% carbomer, alternatively from about 0.5% to about 6% carbomer, alternatively from about 0.7% to about 3% carbomer, and alternatively from about 0.9% to about 1.5% carbomer. Examples of additional carbomers can be found in U.S. Pat. No. 2,798,053.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

Brookfield Viscosity Test

The viscometer is Brookfield viscometer, Model ½ RVT, with a Brookfield "Heliopath"stand (available from Brookfield Engineering Laboratories, Middleboro, Mass.). The spindle is a conventional "E-series" T-shaped spindle. The viscometer is placed on the Heliopath stand and leveled via spirit levels. The E spindle is attached, and the viscometer is set to 2.5 RPM while it is running The viscosity is measured after 1 minute and the temperature is constant at 25° C. The "Brookfield Unit" in which results obtained from this method have traditionally been expressed is simply the direct readout of the instrument under standard conditions, i.e., using the "E" spindle at 2.5 RPM, or calculated equivalent.

pH Test Method

First, calibrate the Thermo Scientific Orion 320 pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

The pH of the liquid medication is measured using the calibrated pH meter at ambient temperature.

Phase Separation Method

After the toothpaste is made, 25 grams of the composition is placed in a polypropylene speed mix jar (max 40 SpeedMixer™ contain available from FlackTek™ Inc.) with a screwed lid screwed hand tight. Then, the container is placed in an oven (Espec™ LHV-113 Temperature and Humidity Cabinet was used here) at 40° C. for about 8 hours. Then, the container is removed and it is observed to see if any phase separation was visually perceptible.

EXAMPLES

|  | Ex. 1 (wt. %) | Ex. 2 (wt. %) | Ex. 3 (wt. %) | Ex. 4 (wt. %) |
|---|---|---|---|---|
| Water | 51.89 | 59.67 | 53.62 | 49.59 |
| Lanette ® W[1] | 12.00 | — | — | — |
| Cold Dispersible Fatty Amphiphile[2] | — | 6.00 | 12.00 | 16.00 |
| Sodium Lauryl Sulfate Powder | 2.50 | 1.50 | 1.50 | 1.50 |
| SepiMAX ™ ZEN | 0.60 | — | — | — |
| Hydrogen Peroxide (35% Ultra Cosmetic) | 8.57 | 8.57 | 8.57 | 8.57 |
| Sodium Fluoride | 0.24 | — | — | — |
| Sodium Monofluorophosphate | — | 0.76 | 0.76 | 0.76 |
| Sodium Acid Pyrophosphate | 0.500 | 1.00 | 1.00 | 1.00 |
| Dibasic Sodium Phosphate USP | 0.20 | 0.20 | 0.25 | 0.28 |
| Sucralose | 0.50 | 0.30 | 0.30 | 0.30 |
| Potassium Nitrate USP | 5.00 | 5.00 | 5.00 | 5.00 |
| Tospearl ® 145[3] | 15.00 | — | — | — |
| Calcium Pyrophosphate | — | 15.00 | 15.00 | 15.00 |
| Flavor | 3.00 | 2.00 | 2.00 | 2.00 |

[1] Lanette ® W is mixture (40:40:10) of cetyl alcohol/stearyl alcohol/sodium lauryl sulfate and is available from BASF Corp
[2] The cold dispersible fatty amphiphile is 40% cetyl alcohol, 40% stearyl alcohol, 10% sodium lauryl sulfate, and 10% sodium acrylate/sodium acryloyl dimethyl daurate copolymer.
[2] Polymethyl organosiloxane particles, more specifically polymethyl organosiloxane silicone resin particles, available from Momentive ™ Performance Materials, New York Example 1 was made as follows. A jacketed mix tank was set to 85° C. Water and Lanette® W were added to the vessel with agitation until the temperature reached 80° C. and a solution that includes melted fatty alcohols and SLS was formed. Then, the polyacrylate crosspolymer-6 was added under agitation to form a substantially homogenous mixture. Then, the heating jacket was reset to 25° C. and the batch was cooled. After the mixture cools, the following materials were added to the vessel: hydrogen peroxide, potassium nitrate, sodium fluoride, sodium acid pyrophosphate, dibasic sodium phosphate and sucralose with agitation and homogenization. Next, the abrasive (Tospearl® 145) was added to the vessel with agitation and the mixture was thoroughly mixed. Once the abrasive had wetted out (i.e. no powders are floating on top of the liquid) the mixture was deaerated. Once the composition was approximately homogenous and approximately all of the air was removed, the flavor the remaining SLS were added to the vessel with agitation. The mixture was then deaerated again. Finally, the first bit of heterogeneous material was removed at the beginning of pumping out of mix tank into a separate container and was discarded as scrap. Once the material began to appear homogeneous, it was collected in a clean container and stored as the final composition. The final composition can then be used to fill tubes, if desired.

Examples 2, 3, and 4 were made as follows. A jacketed mix tank was set to 30° C. The water and 0.1% SLS were added to the vessel with homogenization. Then, the cold dispersible fatty amphiphile was added under agitation to form a substantially homogenous mixture. Then, the following materials were added to the vessel: hydrogen peroxide, sucralose, sodium monofluorophosphate, dibasic sodium phosphate, sodium acid pyrophosphate, and potassium nitrate with agitation and homogenization. Then, the abrasive (calcium pyrophosphate) was added to the vessel with agitation. Once the abrasive had wetted out, the mixture was deaerated. Once the composition was approximately homogenous and approximately all of the air was removed, the remaining SLS, and flavor was added to the vessel with agitation. The mixture was then deaerated again. Next, a sample was removed and the pH was measured. Finally, the first bit of heterogeneous material was removed from the container and was discarded as scrap. Once the material began to appear homogeneous, it was collected in a clean container and stored as the final composition. The final composition can then be used to fill tubes, if desired.

Combinations

A. An oral care composition comprising: (a) a gel network phase comprising a fatty amphiphile and a secondary surfactant; (b) potassium nitrate; (c) a peroxide source selected from the group consisting of hydrogen peroxide, urea peroxide, calcium peroxide, sodium peroxide, zinc peroxide, polyvinylpyrrolidone peroxide complex or combinations thereof; (d) from about 2% to about 25% abrasive, or from about 5% to about 20% abrasive, or from about 7% to about 18% abrasive, or from about 9% to about 16% abrasive; (e) and a fluoride ion source selected from the group consisting of stannous fluoride, sodium fluoride, potassium fluoride, amine fluoride, sodium monofluorophosphate, indium fluoride, amine fluoride, and combinations thereof; wherein phase separation is not visually perceptible as determined by the phase separation method.

B. The oral care composition according to paragraph A wherein the composition comprises from about 0.01% to about 6% peroxide, or from about 0.05% to about 3% peroxide, or from about 0.1% to about 1% peroxide.

C. The oral care composition according to any one of the preceeding paragraphs A-B wherein the abrasive is selected from the group consisting of polyorganosilsequioxane particles, calcium pyrophosphate, dicalcium phosphosphate, calcium phosphate, strontium carbonate, barium sulfate, fused silica, or combinations thereof.

D. The oral care composition according any one of the preceding paragraphs A-C wherein the composition further comprises an AMPS polymer, co-polymer, and/or crosspolymer wherein the AMPS polymer, co-polymer, and/or crosspolymer is selected from the group consisting of hydroxyethyl acrylate/sodium acryloyldimethyl taurate copolymer, ammonium acryloyldimethyl taurate/vinyl pyrrolidone copolymer, ammonium acryloyldimethyltaurate/beheneth-25 methacrylate crosspolymer, sodium acrylate/sodium acryloyldimethyltaurate copolymer, acrylamide/sodium acryloyldimethyltaurate copolymer, polyacrylate crosspolymer-6, and combinations thereof.

E. The oral care composition any one of the preceding paragraphs A-D wherein the composition is substantially free of carrageenan.

F. The oral care composition according to any one of the preceding A-E wherein the composition comprises from about 3% to about 17% fatty amphiphile, or from about 5% to about 15% fatty amphiphile, or from about 7% to about 13% fatty amphiphile, or from about 10% to about 11.5% fatty amphiphile.

G. The oral care composition according to any one of the preceding paragraphs A-F wherein the fatty amphiphile comprises a fatty alcohol selected from the group consisting of cetyl alcohol, stearyl alcohol, and combinations thereof.

H. The oral care composition according to any one of the preceding paragraphs A-G wherein the composition has a viscosity from about 5 BKUs to about 70 BKUs, or from about 10 BKUs to about 45 BKUs, or from about 15 BKUs to about 35 BKUs, or from about 18 BKUs to about 30 BKUs.

I. The composition according to any one of the preceding paragraphs A-F wherein the composition further comprises from about 15% to about 95% water, or from about 25% to about 70% water, or from about 30% to about 50% water, or from about 32% to about 45% water.

J. The composition according to any one of the preceding paragraphs A-G wherein the composition can contain from about 1% to about 15% secondary surfactant, or from about 2% to about 10% secondary surfactant, or from about 4% to about 8% secondary surfactant, or from about 5% to about 7.5% secondary surfactant.

K. An oral care composition comprising: (a) a gel network phase comprising from about 1% to about 20% cold dispersible fatty amphiphile, or from about 3% to about 17% cold dispersible fatty amphiphile, or from about 5% to about 16% cold dispersible fatty amphiphile; (b) potassium nitrate; (c) a peroxide source selected from the group consisting of hydrogen peroxide, urea peroxide, calcium peroxide, sodium peroxide, zinc peroxide, polyvinylpyrrolidone peroxide complex or combinations thereof; (d) from about 2% to about 25% abrasive, or from about 5% to about 20% abrasive, or from about 7% to about 18% abrasive, or from about 9% to about 16% abrasive; (e) and a fluoride ion source selected from the group consisting of stannous fluoride, sodium fluoride, potassium fluoride, amine fluoride, sodium monofluorophosphate, indium fluoride, amine fluoride, and combinations thereof; wherein the oral care composition comprises from about 3% to about 17% fatty amphiphile, or from about 5% to about 15% fatty amphiphile, or from about 7% to about 13% fatty amphiphile, or from about 10% to about 11.5% fatty amphiphile; wherein phase separation is not visually perceptible as determined by the phase separation method.

L. The oral care composition according to paragraph K wherein the composition comprises from about 0.01% to about 6% peroxide, or from about 0.05% to about 3% peroxide, or from about 0.1% to about 1% peroxide.

M. The oral care composition according to any one of the preceeding paragraphs K-L wherein the abrasive is selected from the group consisting of polyorganosilsequioxane particles, calcium pyrophosphate, dicalcium phosphate, calcium phosphate, strontium carbonate, barium sulfate, fused silica, or combinations thereof.

N. The oral care composition any one of the preceding paragraphs K-M wherein the composition is substantially free of carrageenan.

O. The oral dosage form according to any one of the preceding paragraphs K-N wherein the cold dispersible fatty amphiphile comprises one or more straight or branched carbon chains from about C8 to about C25, or from about C12 to about C22.

P. The oral care composition any one of the preceding paragraphs K-O wherein the cold dispersible fatty amphiphile comprises 40% cetyl alcohol, 40% stearyl alcohol, 10% sodium lauryl sulfate, and 10% sodium acrylate/sodium acryloyl dimethyl taurate copolymer.

Q. The oral care composition according to paragraph K-P wherein the fatty amphiphile comprises a fatty alcohol selected from the group consisting of cetyl alcohol, stearyl alcohol, and combinations thereof.

R. The oral care composition according to any one of the preceding paragraphs K-Q wherein the cold dispersible fatty amphiphile comprises: (a) a fatty amphiphile; (b) a surfactant; and (c) a 2-acrylamido-2-methylpropane sulfonic acid (AMPS) polymer; wherein the weight ratio of fatty amphiphile to surfactant is from about 2:1 to 25:1, or from about 4:1 to about 15:1, or from about 6:1 to about 9:1.

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   a. a gel network phase comprising a cold dispersible fatty amphiphile and a secondary surfactant, wherein the cold dispersible fatty amphiphile comprises
      i. about 40%, by weight of the cold dispersible fatty amphiphile, of cetyl alcohol,
      ii. about 40%, by weight of the cold dispersible fatty amphiphile, of stearyl alcohol,
      iii. about 10%, by weight of the cold dispersible fatty amphiphile, of sodium lauryl sulfate, and
      iv. about 10%, by weight of the cold dispersible fatty amphiphile, of a sodium acrylate/sodium acryloyl dimethyl taurate copolymer;
   b. potassium nitrate;
   c. a peroxide source selected from the group consisting of hydrogen peroxide, urea peroxide, calcium peroxide, sodium peroxide, zinc peroxide, polyvinylpyrrolidone peroxide complex and combinations thereof;
   d. an abrasive; and
   e. a fluoride ion source selected from the group consisting of stannous fluoride, sodium fluoride, potassium fluoride, amine fluoride, sodium monofluorophosphate, indium fluoride, amine fluoride, and combinations thereof.

2. The composition of claim 1, wherein the composition comprises from about 0.1% to about 8%, by weight of the dentifrice composition, of the peroxide.

3. The composition of claim 1, wherein the composition comprises less than about 0.1%, by weight of the dentifrice composition, of carrageenan.

4. The composition of claim 1, wherein the composition comprises from about 3% to about 17%, by weight of the dentifrice composition, of the cold dispersible fatty amphiphile.

5. The composition of claim 1, wherein the composition has a viscosity from about 10 BKUs to about 45 BKUs.

6. The composition of claim 1, wherein the composition comprises from about 25% to about 70%, by weight of the dentifrice composition, of water.

7. The composition according claim 1, wherein the composition comprises from about 1% to about 15%, by weight of the dentifrice composition, of the secondary surfactant.

8. The composition of claim 1, wherein the abrasive comprises polyorganosilsequioxane particles, calcium pyrophosphate, dicalcium phosphosphate, calcium phosphate, strontium carbonate, barium sulfate, fused silica, or combinations thereof.

* * * * *